(12) United States Patent
Gupta et al.

(10) Patent No.: US 11,441,994 B2
(45) Date of Patent: Sep. 13, 2022

(54) METHOD AND SYSTEM FOR IN-SILICO DESIGN OF SKIN ELECTROPORATION

(71) Applicant: Tata Consultancy Services Limited, Mumbai (IN)

(72) Inventors: Rakesh Gupta, Pune (IN); Beena Rai, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1084 days.

(21) Appl. No.: 16/046,239

(22) Filed: Jul. 26, 2018

(65) Prior Publication Data

US 2019/0033197 A1    Jan. 31, 2019

(30) Foreign Application Priority Data

Jul. 27, 2017  (IN) .............................. 201721026791

(51) Int. Cl.
| | |
|---|---|
| *G01N 15/08* | (2006.01) |
| *G01N 33/00* | (2006.01) |
| *A61N 1/32* | (2006.01) |
| *G16H 50/50* | (2018.01) |
| *A61N 1/04* | (2006.01) |

(52) U.S. Cl.
CPC ......... *G01N 15/0806* (2013.01); *A61N 1/327* (2013.01); *G01N 15/088* (2013.01);
(Continued)

(58) Field of Classification Search
CPC .... G01N 15/00; G01N 15/08; G01N 15/0806; G01N 15/088; G01N 2015/0833;
(Continued)

(56) References Cited

U.S. PATENT DOCUMENTS

| | | | |
|---|---|---|---|
| 8,234,074 B2 * | 7/2012 | Lopez .................. | G16C 10/00 702/19 |
| 11,013,917 B2 * | 5/2021 | Housley .................. | A61N 1/30 |

(Continued)

OTHER PUBLICATIONS

Das, C. et al. (Jun. 2016). "The Physics of Stratum Corneum Lipid Membranes," *Philosophical Transactions of the Royal Society A: Mathematical, Physical, & Engineering Sciences*, vol. 374, issue 2072; pp. 1-17.

(Continued)

*Primary Examiner* — Nguyen Q. Ha
(74) *Attorney, Agent, or Firm* — Finnegan, Henderson, Farabow, Garrett & Dunner LLP (57) ABSTRACT

A system and method for testing of skin electroporation using simulations of human skin has been described. The system is using a simulation protocol to provide an in-silico design of skin's upper layer stratum-corneum (SC) at molecular level. This model is then further used to design the skin electroporation strategy. An external electric field was applied across the lipid bilayer to form a pore in the lipid bilayer. The pore size and pore growth rate was calculated depending on the applied external electric field. The generated pore was then stabilized by varying the external electric field. Further, on removing the external electric field, the reformation of lipid bilayer and self-healing of human skin was also achieved. In another embodiment, the system is also configured to perform the virtual testing of a drug permeation through skin in presence of external electric field.

13 Claims, 10 Drawing Sheets

(52) U.S. Cl.
CPC ........... G16H 50/50 (2018.01); *A61N 1/0412* (2013.01); *G01N 2015/0833* (2013.01)

(58) Field of Classification Search
CPC ........ G01N 33/00; G01N 33/48; G01N 33/50; A61N 1/04; A61N 1/0412; A61N 1/32; A61N 1/327; G16H 50/50
See application file for complete search history.

(56) References Cited

U.S. PATENT DOCUMENTS

2005/0282284 A1* 12/2005 Rubinsky ............... C12M 35/02
435/459
2016/0361109 A1* 12/2016 Weaver ................ A61N 1/0412

OTHER PUBLICATIONS

Notman, R. et al. (Nov. 2008). "Simulations of Skin Barrier Function: Free Energies of Hydrophobic and Hydrophilic Transmembrane Pores in Ceramide Bilayers," *Biophysical Journal*, vol. 95; pp. 4763-4771.

Neyts, E.C. et al. (Jun. 2014). "Computer simulations of plasma-biomolecule and plasma-tissue interactions for a better insight in plasma medicine," *Journal of Physics D: Applied Physics*, vol. 47; 19 pages.

Dai, X. et al. (Aug. 2016). "Effects of Concentrations on the Transdermal Permeation Enhancing Mechanisms of Borneol: A Coarse-Grained Molecular Dynamics Simulation on Mixed-Bilayer Membranes," *International Journal of Molecular Sciences*, vol. 17, issue 8, pp. 1-15.

* cited by examiner

METHOD AND SYSTEM FOR IN-SILICO DESIGN OF SKIN ELECTROPORATION

PRIORITY CLAIM

This U.S. patent application claims priority under 35 U.S.C. § 119 to: India Application No. 201721026791, filed on Jul. 27, 2017. The entire contents of the aforementioned application are incorporated herein by reference.

TECHNICAL FIELD

The embodiments herein generally relates to the field of human skin modeling and simulation, and, more particularly, to a method and system for in-silico design and testing of skin electroporation.

BACKGROUND

Skin, the largest organ of our body protects us from the attack of foreign pathogens and provides barrier to the permeation of many harmful molecules and maintains the hydration level of tissues. The outer layer of skin, also known as Stratum Corneum (SC) is mainly responsible for these barrier properties.

The delivery of drugs through the skin provides a convenient route of administration because of high surface area of skin and can typically be self-administered. Transdermal drug delivery offers numerous advantages over conventional drug delivery system such as absence of gastric irritation, avoidance of erratic absorption, non-invasive in nature, high surface area of skin and as well as improvement in patient compliance.

The Stratum Corneum is highly selective in nature and typically allows only relatively lipophilic compounds to diffuse into the inner layers of skin. The Stratum Corneum is highly hydrophobic in nature and the transport of molecules across skin occurs primarily by passive diffusion and mostly through lamellar lipid matrix. Most of the drugs and protein, which are in hydrophilic in nature, cannot breach this barrier.

There are several techniques have been developed and used widely over the years to enhance the drug permeation by breaching the barrier function. These techniques are broadly classified in two categories based on their working principle (a) passive transport through chemical penetration enhancers, liposomes and (b) active methods such as electroporation, iontophoresis, sonophoresis and thermophoresis. The active methods such as electroporation, iontophoresis, sonophoresis and thermophoresis use external energy source (electric current, ionic flux etc.) and creates the temporary nanometer sized pores in the SC which further felicitate facilitate the permeation of molecules.

Electroporation, is mostly referred to the temporary perturbation of the skin by using the application of high voltage in the form of pulses for short duration of time ($\mu$s to ms). Electroporation was originally used to breach cells with macromolecules (such as DNA) by altering their cell lipid membranes in a reversible manner. Later on, this technique was used for application in transdermal drug delivery for delivering macromolecules such as peptides and proteins. The electroporation of skin requires higher voltages (>50-100 V) as compared to electroporation of cell membranes. Electroporation pulses are broadly classified into two regimes namely short and long pulses.

Since last two decades, researchers have carried out numerous electroporation experiments for delivery of both small and macromolecules through skin. The efforts includes, delivery of various ionic, non-ionic, neutral and charged drug molecules through skin (rat, mouse and human) using low to high varying electric field. Electroporation has also been widely used in experimental settings for gene transfer into and through the skin. Despite of having so many experimental studies, the underlying molecular mechanism/s which induce the structural changes in the skin during electroporation are still not well understood. However, it has been hypothesized that water pores form in the skin on application of high voltage pulses. It is also reported that skin permeability increased significantly (up to four orders of magnitude) when voltage drop across the skin SC layer crossed 30 V and it was hypothesized that modification of skin lipid structure occurred due to the interaction between the water dipole and the electric field. To understand the macroscopic mechanism of electroporation, there are some mathematical transport model of skin electroporation have been developed by combining passive transport models with electroporation models. Moreover, not a single study of molecular mechanism of electroporation of skin SC lipid matrix has not been reported. Molecular simulations provide a convenient way to understand permeation and dynamics processes of skin and yield important physical insights at molecular level which could not be obtain from experiments because of associated time and length scale.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for testing of skin electroporation using simulations of human skin in absence and presence of external electric field. The system comprises a first input module, a second input module, a memory and a processor. The first input module provides a molecular model of stratum corneum layer of the human skin, wherein the stratum corneum layer comprises a lipid bilayer. The second input module sets a plurality of parameters for creating an equilibrium environment for the simulations. The processor further configured to perform the steps of: applying an external electric field, wherein the application of the external electric field results in the generation of a pore inside the lipid bilayer of the stratum corneum layer; measuring the radius of the pore along across the bilayer based on the applied external electric field; stabilizing the radius of the pore by varying the applied external electric field; and, removing the external electric field, wherein the removal of external electric field results in the reformation of the lipid bilayer and self-healing of human skin.

In another aspect the embodiment here provides a method for testing of skin electroporation using simulations of human skin. Initially, a molecular model of stratum corneum layer of the human skin is provided, wherein the stratum corneum layer comprises a lipid bilayer. In the next step, a plurality of parameters are set for creating an equilibrium environment for the simulations. In the next step, an external electric field is applied across the lipid bilayer, wherein the application of the external electric field results in the generation of pore/s inside the lipid bilayer of the stratum corneum layer. The radius of the pore across the bilayer is then measured based on the applied external electric field. The radius of the pore is then stabilized by varying the applied external electric field. And finally the external electric field is removed, wherein the removal of external electric field results in the reformation of the lipid bilayer and self-healing of human skin.

In yet another aspect, a non-transitory computer-readable medium having embodied thereon a computer program for executing a method for testing of skin electroporation using simulations of human skin. Initially, a molecular model of stratum corneum layer of the human skin is provided, wherein the stratum corneum layer comprises a lipid bilayer. In the next step, a plurality of parameters are set for creating an equilibrium environment for the simulations. In the next step, an external electric field is applied across the lipid bilayer, wherein the application of the external electric field results in the generation of pore/s inside the lipid bilayer of the stratum corneum layer. The radius of the pore across the bilayer is then measured based on the applied external electric field. The radius of the pore is then stabilized by varying the applied external electric field. And finally the external electric field is removed, wherein the removal of external electric field results in the reformation of the lipid bilayer and self-healing of human skin.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Referring now to the drawings, and more particularly to FIG. 1 through FIG. 9, where similar reference characters denote corresponding features consistently throughout the figures, there are shown preferred embodiments and these embodiments are described in the context of the following exemplary system and/or method.

Figure 1:
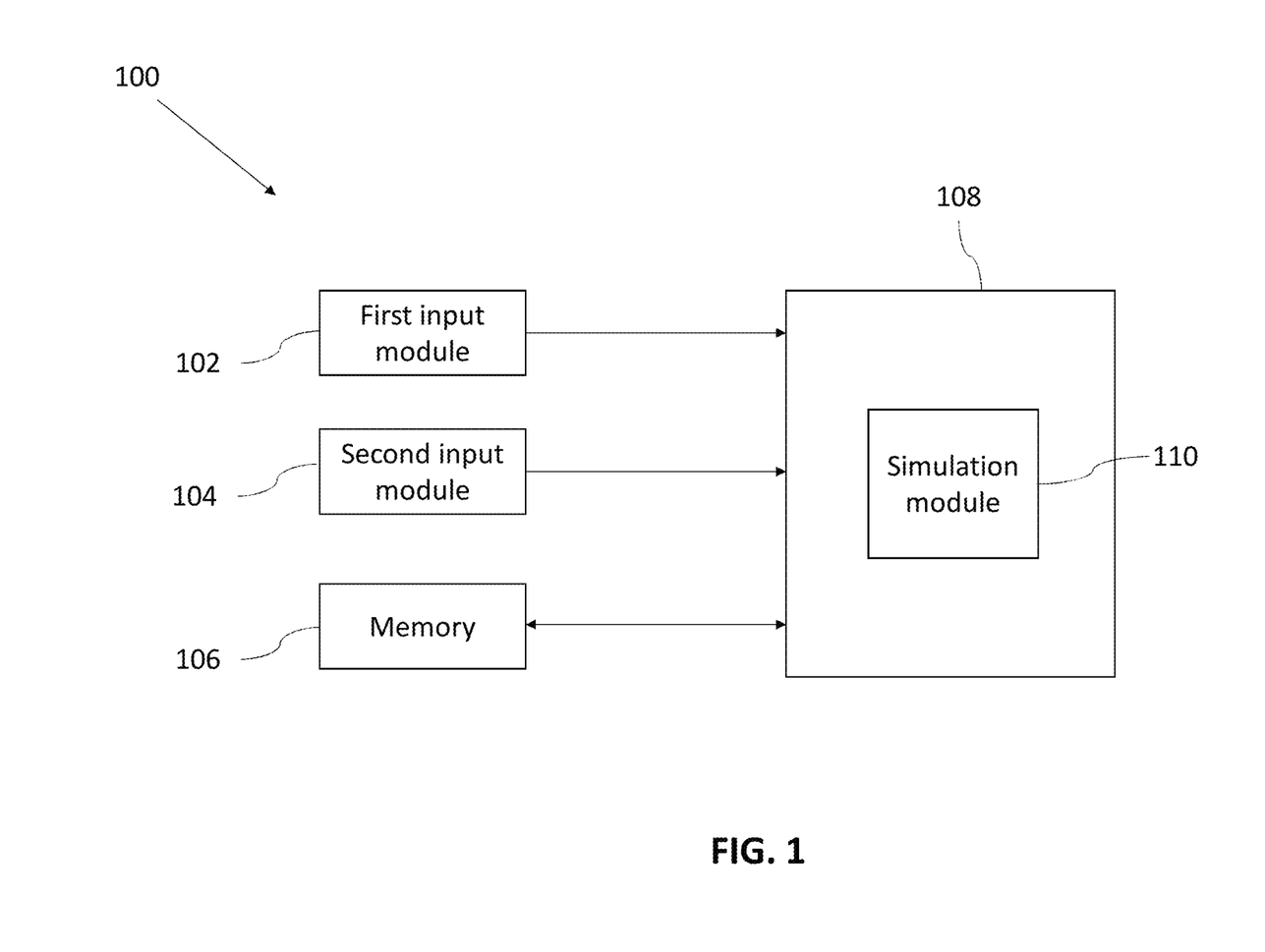
FIG. 1 illustrates a block diagram for testing of skin electroporation using simulations of human skin according to an embodiment of the present disclosure.

According to an embodiment of the disclosure, a system 100 for testing of skin electroporation using simulations of human skin is shown in the block diagram of FIG. 1. The system 100 uses a molecular level resolution and model of realistic skin lipid matrix. The system 100 uses a simulation protocol to provide in-silico design of skin's upper layer stratum-corneum (SC) at molecular and macroscopic level. This model is then further used to design the skin electroporation strategy. In another embodiment, the system 100 is also configured to perform the virtual testing of a drug permeation through skin in presence of external electric field.

According to an embodiment of the disclosure, the system 100 consists of a first user interface 102, a second user interface 104, a memory 106 and a processor 108 as shown in the block diagram of FIG. 1. The processor 108 is in communication with the memory 106. The processor 108 configured to execute a plurality of algorithms stored in the memory 106. The processor 108 further includes a plurality of modules such as a simulation module 110 for performing various functions.

According to an embodiment of the disclosure the first input module 102 is configured to provide a molecular model of stratum corneum layer of the human skin as an input to the processor 108. And the second input module 104 is configured to set a plurality of parameters for creating an equilibrium environment for the simulations. The first and the second input module 102 and 104 are operated by a user. The first input module 102 and the second input module 104 are a kind of user interface. In another embodiment, the system 100 may include only one input module serving both the functions. The user interface/input modules can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

The topmost layer of the skin is known as stratum corneum (SC). The stratum corneum is made up of 15-20 layers of flat dead cell shells known as corneocytes, which are interconnected by a lipid lamellar bilayer structure in a crystalline-gel phase. The corneocytes and lipid matrix are arranged in brick and mortar fashion respectively. The skin barrier function is mostly determined by the packing of lipid matrix because corneocytes are almost impermeable in nature. The lipid matrix is a heterogeneous mixture of long chain Ceramides (CER), cholesterol (CHOL) and free fatty acids (FFA) in certain ratio. Skin lipid matrix is very complex in nature and consist almost 300 different types of Ceramides. In order to simulate a realistic lipid bilayer of SC, most abundant Ceramide, CER-NS, and free fatty acid (chain length of 24) are used.

According to an embodiment of the disclosure, the second input module 104 is configured to set the plurality of parameters to achieve an equilibrium environment for performing the simulations. The plurality of parameters comprises one or more of a skin temperature, a pressure, force field parameters of skin lipid interaction, applied electric field or temperature coupling. The plurality parameters are not limited to above mentioned parameters, various other parameters can also be adjusted to achieve the equilibrium.

In an embodiment of the disclosure, the temperature was controlled at a skin temperature of ~310 K, using the Berendsen (equilibration run) and Nose-Hover (production run) thermostat with a time constant of 2 ps. Pressure was controlled by Berendsen and Parrinello-Rahman barostat with a time constant of 6 and 12 ps, respectively and compressibility of $4.0\times10^{-5}$ bar-1 in equilibrium and production run respectively with semi-isotropic coupling. The pressure was controlled in XY and Z direction independently in order to obtain the tension free bilayer. All the bonds in lipid and solute molecules were constrained using LINCS algorithm while SETTLE algorithm was used for water. A time step of 2 fs was used for all simulations. A cut off of 1.2 nm was used for Vander Waal and electrostatic interactions. The long range electrostatic interactions were computed using particle mesh Ewald (PME) method. The bilayer systems were periodic in all three directions. The configuration was sampled at every 10 ps in a production run. The neighbor list was updated at every 10 steps. These parameters can be changed accordingly depending on various requirements, one should not only adhere to these parameters. The use of different parameters is well within the scope of this disclosure.

Figure 2:
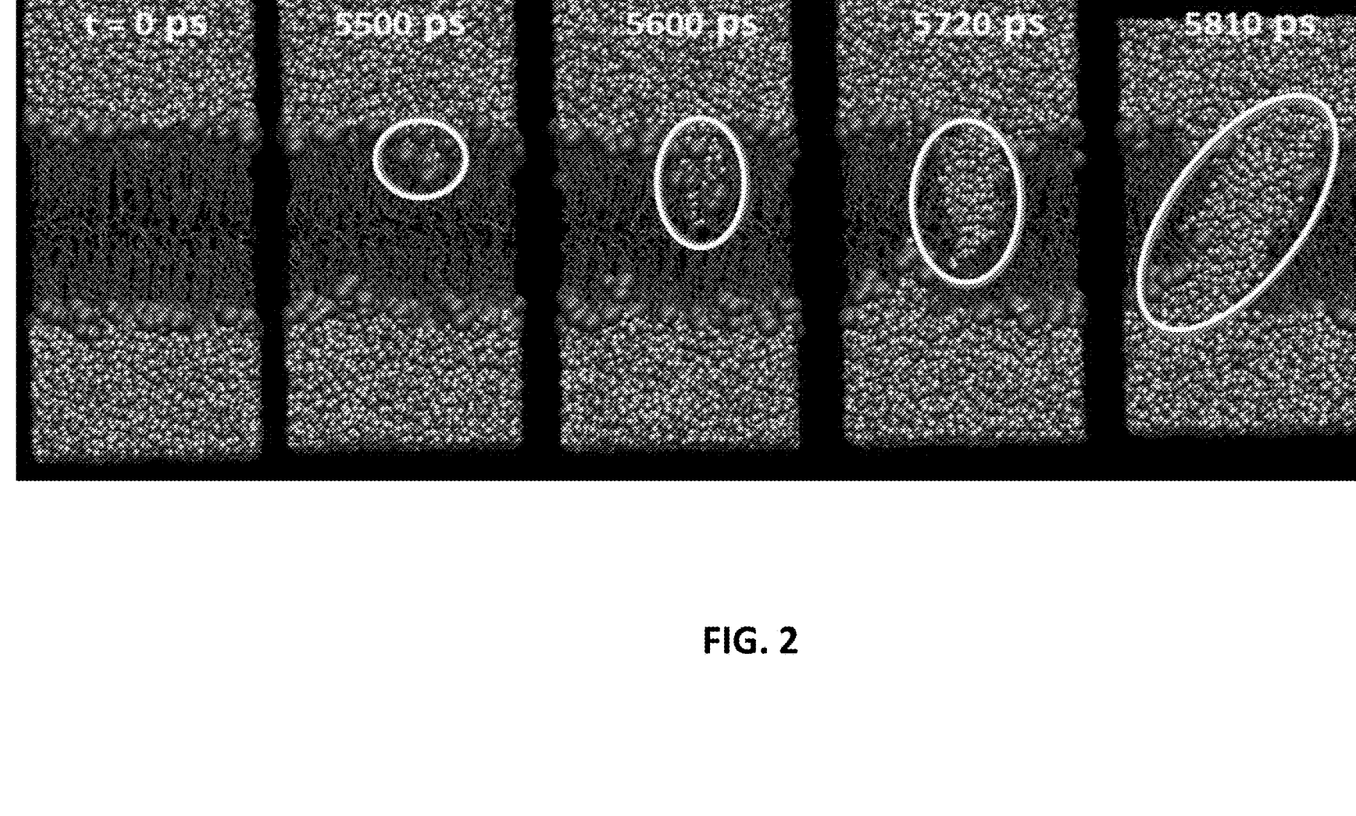
FIG. 2 shows a side view of the lipid bilayer showing the generation of pore in a timeline according to an embodiment of the disclosure.

According to an embodiment of the disclosure the system 100 is further includes the simulation module 110. The simulation module is configured to apply an external electric field across the bilayer of the human skin. In an example, the simulation module 110 performs all simulations in NVT and NPT ensemble using the GROMACS molecular dynamics package. Though use of any other simulation tool is well within the scope of this disclosure. The application of external electric field results in the generation of a pore inside the lipid bilayer of the stratum corneum layer as shown in FIG. 2. The external electric field was applied in the Z direction (normal to the XY plane of bilayer). The pore formation occurs after a certain critical electric field is crossed, also known as threshold field. All the fields, above the threshold field, do form pore in the bilayer and known as porating fields.

Figure 9:
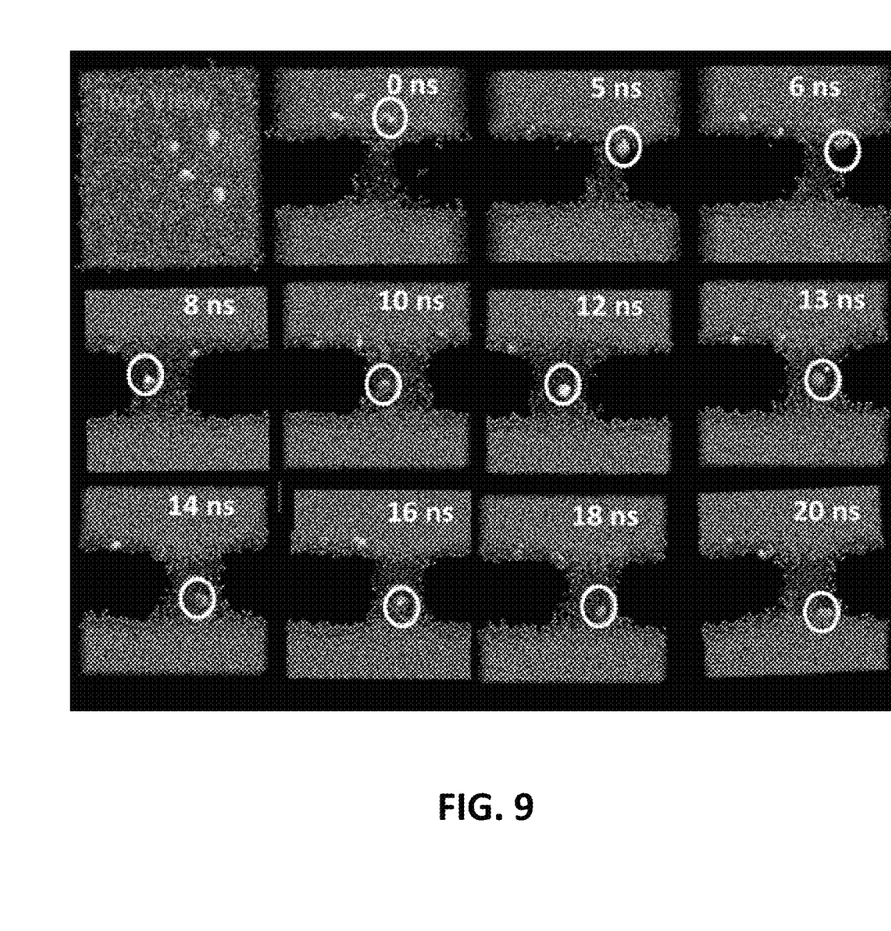
FIG. 9 shows a side view of the delivery of a drug across the lipid bilayer in a timeline according to an embodiment of the disclosure.

According to an embodiment of the disclosure, the system 100 is configured to calculate the size of the pore. The size is measured in terms of the radius of the pore across the bilayer based on the applied external electric field. The pore radius changes along the bilayer normal Z. The pore size is not equal in both X and Y direction. To calculate the pore size of the bilayer, the bilayer was projected on the X and Y plane separately. For the purpose of calculation a molecule was delivered in the pore as shown in FIG. 9. The maximum and minimum coordinate of molecule in each X and Y direction was calculated. The difference of maximum and minimum coordinate in each X and Y direction gives the pore size $R_x$ and $R_y$ in X and Y direction respectively. The pore radius ($R=\sqrt{R_x R_y}$) calculated using geometric mean of $R_x$ and $R_y$. In an embodiment, the pore size is between 3 nanometer to 4 nanometer. Though it should be appreciated that the pore size can be made more than 4 nanometer by changing the applied both the external electric field and time of application of electric field.

According to an embodiment of the disclosure, the system 100 is further configured to stabilize the radius of the pore by varying the applied external electric field. The external electric field is applied in terms of voltage in the range of 100 to 1500 Volts. The applied voltage should be chosen in such a way that the bilayer should not rupture. A very high voltage may also lead to the burning of the skin. The stratum corneum is made of up approximately 100 bilayer membranes in series and temporary increase in the permeability of stratum corneum usually takes place when voltages drop across stratum corneum reaches 30-100 V (applied voltages 100-1500 V). Which in turns, for each skin bilayer the electroporation voltage spectrum 0.3-1.0 V is almost similar to voltage used in cell electroporation. The molecular dynamic simulation of electroporation of planar lipid membrane can be performed using two techniques a) direct application of electric field across the bilayer normal and b) charge imbalance method. The present embodiment is using the direct application of electric field along the lipid bilayer method to capture the electroporation of skin SC lipid bilayer. The electric field of strength, E, is applied perpendicular to the lipid bilayer plane (here it is XY plane). This is implemented by adding additional force (F=E.qi) to all the charged atoms "i".

According to an embodiment of the disclosure, the system 100 is also configured to calculate the pore growth rate and poration time. The pore growth rate was determined based on the change in the pore radius in predefined time interval. The snapshots of each bilayer was taken at two different simulation time. The evolution of the pore size along the bilayer normal z, calculated using the procedure mentioned above. Here, RxE Pore radius in x direction in the last frame, RyE Pore radius in y direction in the last frame, RE Pore radius in the last frame, RxS Pore radius in x direction in the initial frame, RyS Pore radius in y direction in the initial frame, RS Pore radius in the initial frame. The growth rate has been calculated using the following equation:

$$G = \frac{(RE - RS)}{\Delta t}$$

Where, G is growth rate of the bilayer pore and $\Delta t$ is difference in time frame.

The optimum values of the combination of applied external electric field and poration time can also be calculated which can be applied safely without burning or rupturing the skin during the pore formation. The optimum value will be changed depending on the size of the drug molecule and type of skin. Based on the experimental results, it can be determined after how much time, the pore will start appearing, and similarly how much more time it will take to grow up to a certain size.

According to an embodiment of the disclosure, the system 100 is also configured to reform the lipid bilayer as shown in FIG. 9. The reformation occurs when the external electric field is removed. The reformation of lipid bilayer also results in self-healing of the human skin. In an example of the present embodiment the pore disappeared with in first ~10-20 ns of the run. The water pore is marked by the white color eclipse in FIG. 9.

Figure 3A:
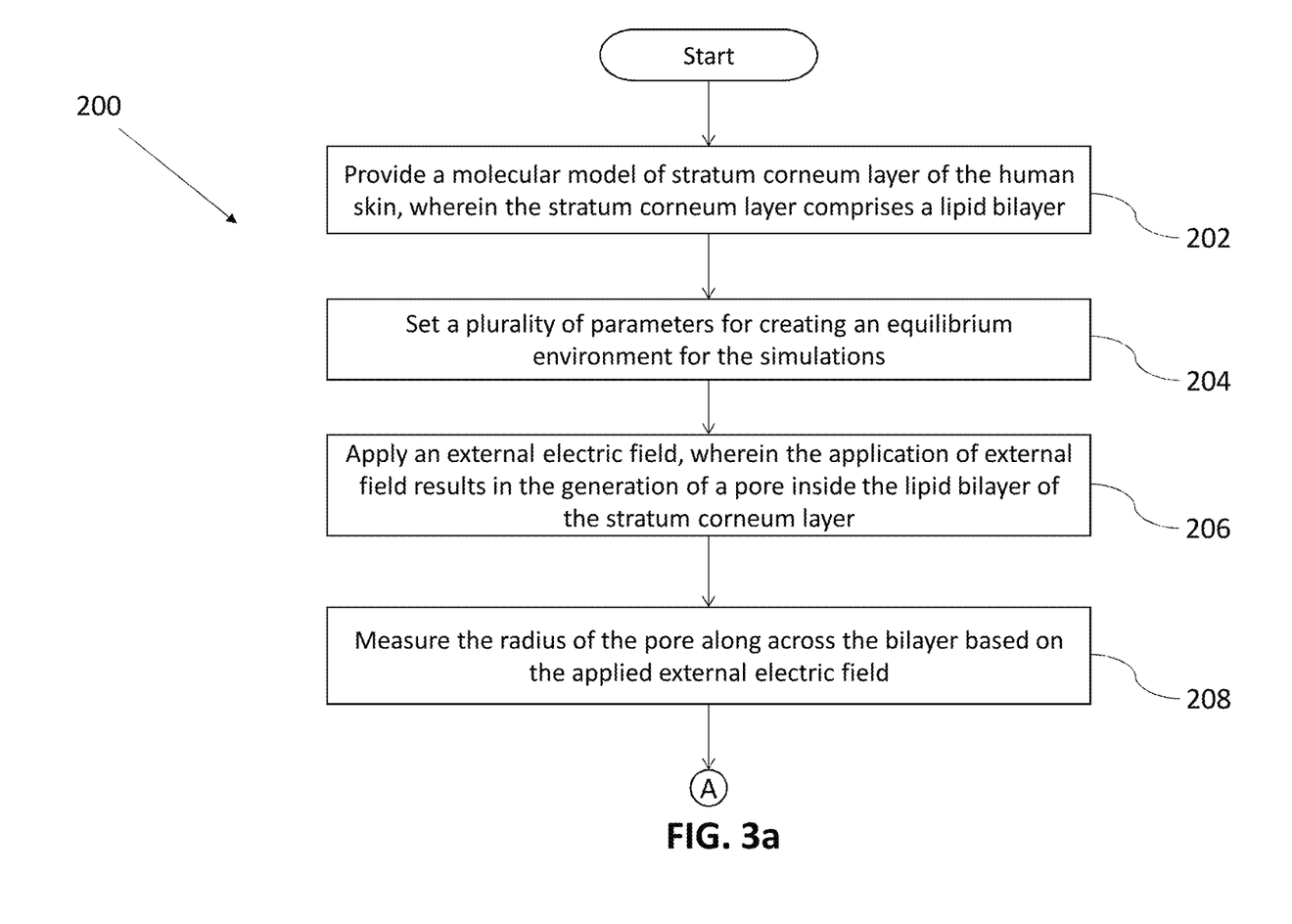
FIG. 3a-3b is a flowchart illustrating the steps involved in testing of skin electroporation using simulations of human skin according to an embodiment of the present disclosure.
Figure 3B:
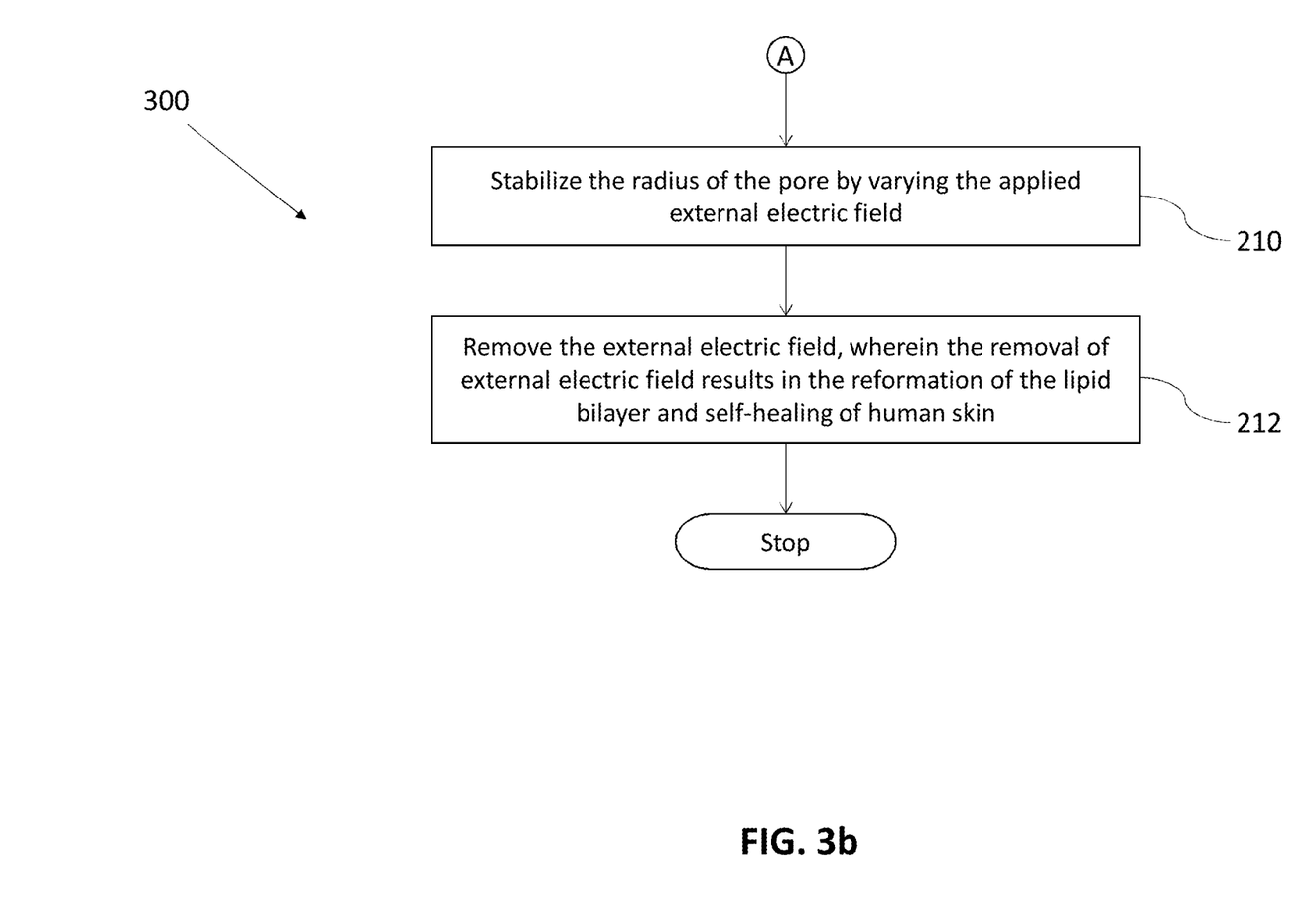

In operation, a flowchart 200 illustrating the steps involved for testing of skin electroporation using simulations of human skin is shown in FIGS. 3a and 3b according to an embodiment of the disclosure. Initially at step 202, a molecular model of stratum corneum layer of the human skin is provided to the processor. The stratum corneum layer comprises a lipid bilayer. In the next step 204, the plurality of parameters are set for creating an equilibrium environment for the simulations. The plurality of parameters include one or more of skin temperature, pressure, force field parameters of skin lipid interaction, applied electric field or temperature coupling etc.

In the next step 206, the external electric field applied across the lipid bilayer. The application of the external electric field results in the generation of a pore inside the lipid bilayer of the stratum corneum layer. At step 208, the radius of the pore across the bilayer is measured based on the applied external electric field. In the next step 210, the radius of the pore is stabilized by varying the applied external electric field. And finally at step 212, the external electric field is removed. The removal of external electric field results in the reformation of the lipid bilayer and self-healing of human skin.

According to an embodiment of the disclosure, the system 100 is also configured to deliver a drug using electroporation. FIG. 9 shows the side view of the process of delivery of drug through the pore along the timeline of 0-20 ns. The chains of lipid molecules are not shown for the purpose of clarity. The CER, CHOL, FFA and drug molecules (white color) are shown. The drug molecule is marked by the white color eclipse. The time given in each snapshots, do represent the kinetics of permeation of the drug molecule through the hydrophilic pore of bilayer. The permeation process is stochastic in nature and exact value of time represented here are not exactly reproducible.

All simulations were carried out in NVT and NPT ensemble using the GROMACS molecular dynamics package. In the present example, the temperature was controlled at a skin temperature of ~ 310 K, using the Berendsen (equilibration run) and Nose-Hover (production run) thermostat with a time constant of 2 ps. Pressure was controlled by Berendsen and Parrinello-Rahman barostat with a time constant of 6 and 12 ps, respectively and compressibility of $4.0 \times 10^{-5}$ bar$^{-1}$ in equilibrium and production run respectively with semi-isotropic coupling. The pressure was controlled in XY and Z direction independently in order to obtain the tension free bilayer. All the bonds in lipid and solute molecules were constrained using LINCS algorithm while SETTLE algorithm was used for water. A time step of 2 fs was used for all simulations. A cut off of 1.2 nm was used for Vander Waal and electrostatic interactions. The long range electrostatic interactions were computed using particle mesh Ewald (PME) method. The bilayer systems were periodic in all three directions. The configuration was sampled at every 10 ps in a production run. The neighbor list was updated at every 10 steps. These parameters can be changed accordingly, one should not only adhere to these parameters. The use of different parameters is well within the scope of this disclosure.

It is postulated that the electroporation induces nano sized to micro sized pores in the lipid bilayer. To capture the effect properly, bigger bilayer patches were used. The smaller patch of skin lipid bilayer (154 lipids (S0), CER-52, CHOL-50 and FFA-52, 40 water molecules per lipid molecule), taken from earlier simulations, was replicated in X and Y direction in order obtain to bigger bilayer patches of 616 (S1) and 2464 lipids (S2). The initial size of each bilayer and number of lipid and water molecules in each bilayer system is showed in Table 1 below. Both of the bigger patches were subjected to NVT run for 20 ns and followed by 200 ns NPT run. Final equilibrated structures were used for further electroporation simulation.

TABLE 1

| System Name | No. of CER | No. of CHOL | No. of FFA | No. of total lipids | No. of water molecules | System Size |
|---|---|---|---|---|---|---|
| S0 | 52 | 52 | 50 | 154 | 5120 | 4.9 nm × 4.9 nm × 11.62 nm |
| S1 | 208 | 208 | 200 | 616 | 20480 | 9.79 nm × 9.79 nm × 11.61 nm |
| S2 | 832 | 832 | 800 | 2464 | 81920 | 19.56 nm × 19.56 nm × 11.62 nm |
| S3 | 104 | 104 | 100 | 308 | 5120 | 4.9 nm × 4.9 nm × 16.52 nm |
| S4 | 128 | 0 | 0 | 128 | 5120 | 4.9 nm × 4.9 nm × 12.34 nm |
| S5 | 64 | 64 | 0 | 128 | 5120 | 4.87 nm × 4.87 nm × 11.22 nm |
| S6 | 84 | 0 | 84 | 168 | 5120 | 4.98 nm × 4.98 nm × 12.15 nm |

Pore Formation in Skin Lipid Bilayer

The bilayer systems, on which the electroporation simulations were performed, are shown in Table 1. The external electric field was applied in the Z direction (normal to the XY plane of bilayer). The pore formation occurs after a certain critical electric field, also known as threshold field. All the fields, above the threshold field, do form pore in the bilayer and known as porating fields. Experimentally it has been shown earlier that the skin permeability decreased several order of magnitude once the trans stratum corneum voltage reached a critical value of 30-100 V. Since stratum corneum is composed of 100's of lamellar bilayer in series, the effective trans-membrane voltage for each bilayer is almost corresponds to 0.3-1.0 V. Based on this background, the experiments were started with electric field of 0.3 V/nm and reached to 1.0 V/nm. To determine the threshold of the electric field, the smallest bilayer system S0 (154 lipids), was used. Since the electroporation process is stochastic in nature at molecular scale, four separate electroporation simulations were performed at each electric field. Initially, the electric field of 0.3 V/nm was applied along the bilayer normal and the simulations were ran for 200 ns. Subsequently, the electric field was increased by 0.1 V/nm in each steps and simulations were ran for 200 ns at each electric field.

Water Pore Stabilization

The water pore size get bigger and bigger in each bilayer system after the application of porating electric field. To stabilize the water pore, the electric field were reduced significantly, once the pore radius almost reached to ~3-4 nm. The water pore stabilization simulations were only performed for system S1. Because, the system S0 was very small in size (~5 nm×5 nm) and pore size of ~3 nm has fully disrupted the bilayer, while system S2 was very big in size and was computationally very challenging. The initial structure of bilayer (having pore size ~3-4 nm) was taken from the electroporation simulation of S1 system at 1.0 V/nm. Since the electroporation process is very stochastic in nature, multiple simulations were run at each applied electric field lower than porating field. The bilayers (five independent S1 systems) were subjected to lower electric field (starting from 0.1 V/nm) and the sustainable electric field was chosen at which the pore survived at least for 50 ns. The applied electric field increased in steps (0.025 V/nm per step) and simulation was run for 50 ns at each step.

Bilayer Reformation

After the application of porating electric fields, the pore formed in bilayer system within ~ 2 ns-100 ns based on applied electric field and bilayer composition. Additional simulations have been performed in order to check, what happens when porating electric field completely removed. These simulation were only performed for system S1. The initial structures (bilayer having pore ~>3 nm) were taken from the electroporation simulation at porating electric field of 0.8, 0.85, 0.9 and 1.0 V/nm. Three independent simulations (20 ns each) were run for each structure (3×4=12 simulations) without application of electric field.

Results

Skin electroporation in S0 system occurred at 5.8 ns on applied of 1.0 V/nm as shown in FIG. 2. FIG. 2 shows the front view of small lipid bilayer (S0) of 154 lipids during one of the electroporation simulation at applied electric field of 1.0 V/nm. The CER, CHOL and FFA are shown in orange, green and blue color respectively. The pore formation starts at ~5500 ps. The water pore is marked by the white color circle. The potential is positive at the top leaflet of the bilayer relative to the bottom leaflet. The time given in each snapshots do represent only the kinetics of the defects developed in the bilayer after application of electric field.

Figure 4:
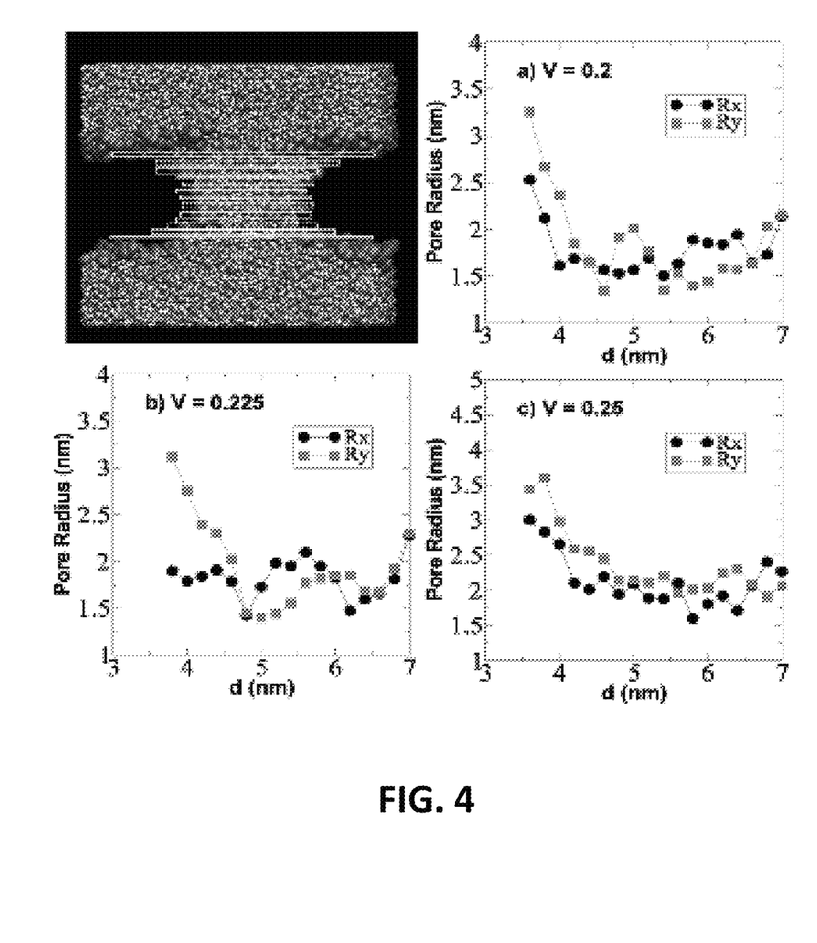
FIG. 4 shows graphical representation of calculation of the pore size of bilayer along the bilayer normal according to an embodiment of the disclosure.

The pore radius changed along the bilayer normal and same was calculated using the newly developed method according to an embodiment of the present disclosure as shown in FIG. 4. FIG. 4 shows the calculation of the pore size of bilayer along the bilayer normal. The bilayer projected in X and Y plane and divided into small bins of 0.2 nm each. Evolution of the pore size along the bilayer normal z in bilayer system (S1).

Figure 5:
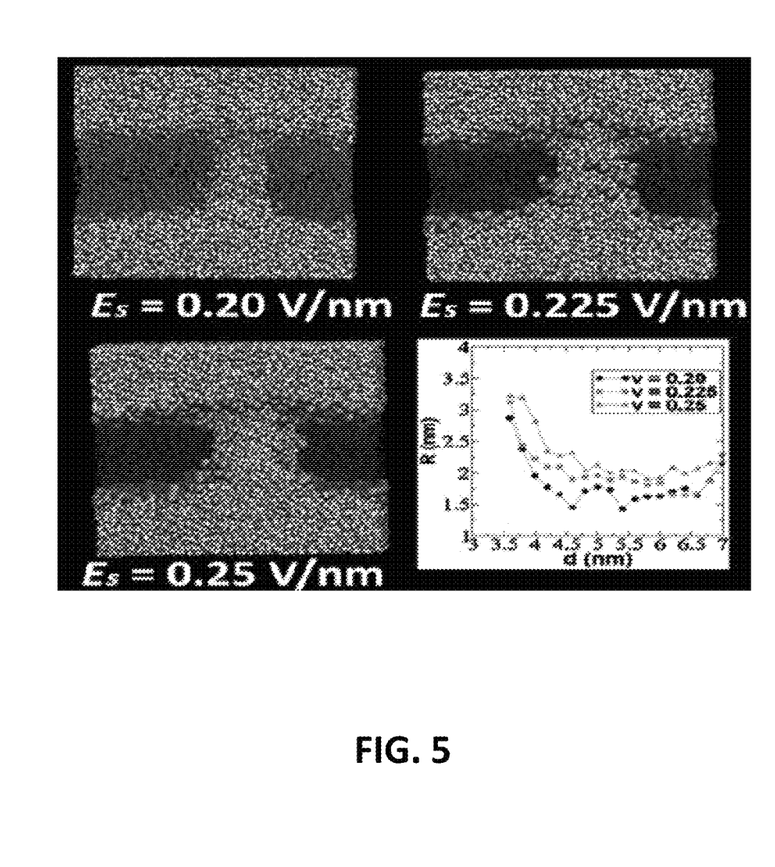
FIG. 5 shows the graphical representation for determining the sustain voltage for stable pore according to an embodiment of the disclosure.

The pore stabilized at electric field of 0.2-0.25 V/nm. The pore size increased with increased sustaining electric field as shown in FIG. 5. FIG. 5 shows the front view of big lipid bilayer (S1) of 616 lipids during one of the electroporation simulation at lower sustain electric field of 0.2, 0.225 and 0.25 V/nm. The potential is positive at the top leaflet of the bilayer relative to the bottom leaflet. Five independent simulations were run for each applied electric field (0.2, 0.225 and 0.25 V/nm) and snapshots of the system, in which pore remained stable, is shown here. The initial pore formed bilayer configuration for these simulation were taken from the electroporation simulations (system S1 at electric field of 1.0 v/nm).

Figure 6:
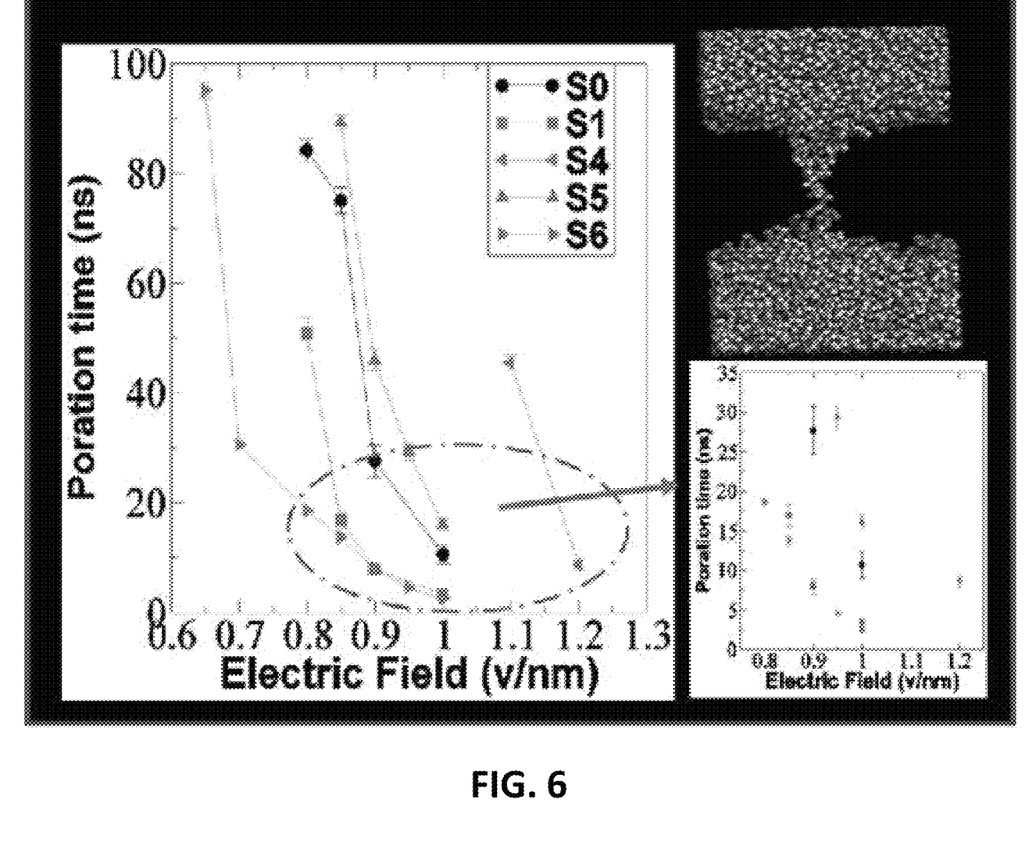
FIG. 6 shows the graphical representation of effect of electric field on the poration time according to an embodiment of the disclosure.

Poration time for system S0 was 84.24±2.11, 75.10±2.32, 27.67±2.99 and 10.71±1.64 ns for applied external electric field of 0.8, 0.85, 0.9 and 1.0 V/nm as shown in FIG. 6. The poration time referred to the time after which water file linked both of the leaflet of the bilayer as shown in the snapshot. At each applied porating electric field, four independent simulations were run. The average of these four runs has been shown here in FIG. 6. The simulations were performed for S0, S1, S4, S5 and S6 systems.

Poration time decreased with increase in the system size for a given porating electric field. Poration time of 10.71±1.64 ns, 3.41±0.45 ns and 1.28±0.21 ns was obtained for system S0, S1 and S2 respectively for applied electric field of 1.0 V/nm as shown in FIG. 6.

The poration time, for a given porating field, was higher in CER (S4) bilayer and lower in CER & FFA (S6) bilayer as shown in FIG. 6.

The threshold electric field was minimum for system S6 (CER & FFA) and maximum for S4 (only CER) and second, for a given applied electric field, the poration time was more in S5 system as compared to S6 system as shown in FIG. 6.

The pore growth depends both on the size of the bilayer and as well as the composition. The pore growth rate was higher in bigger S1 system as compared to S0 system as shown in FIG. 7.

Figure 7:
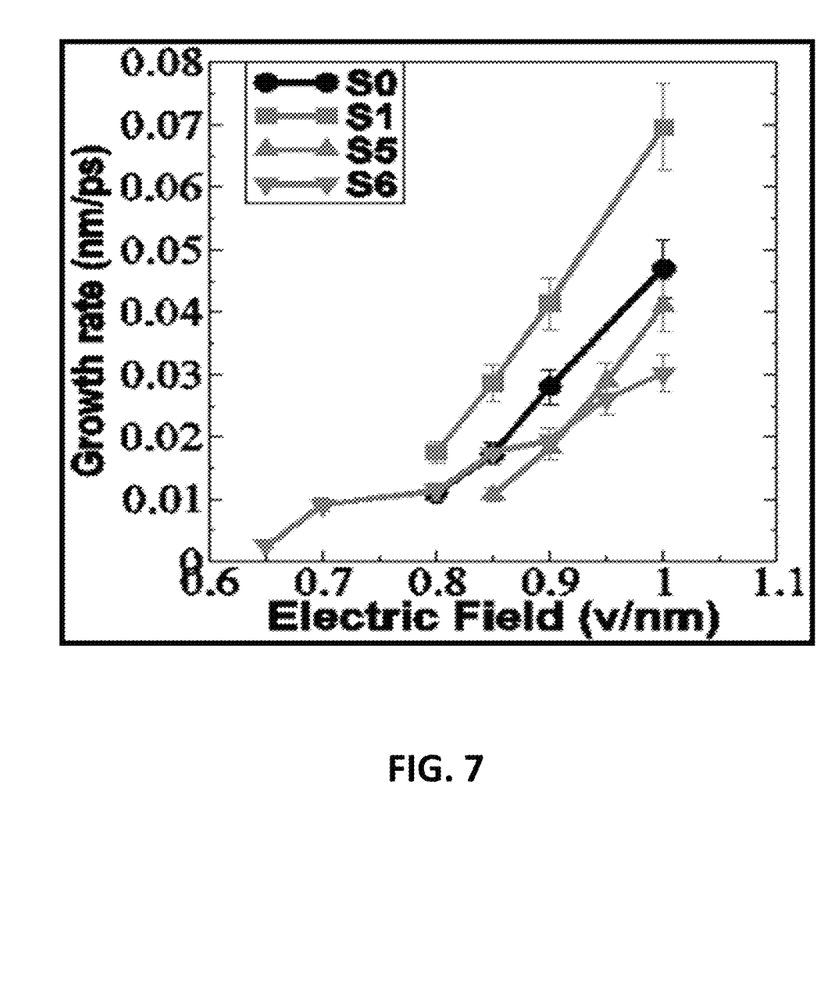
FIG. 7 shows the graphical representation of pore growth rate in bilayer on application of porating electric field according to an embodiment of the disclosure.

For a given porating electric field, the pore growth rate was higher in mixed CER, CHOL & FFA (S0 and S1) bilayer as compared to CER & CHOL and CER & FFA bilayer as shown in FIG. 7. All the fields, above the threshold field, which form pore in the bilayer are referred as porating fields. The pore growth rate were calculated based on the change in the pore radius within given simulation time. The pore growth were calculated for system S0, S1, S5 and S6. At each applied porating electric field, four independent simulations were run. The average of these four runs has been shown here in FIG. 7.

Figure 8:
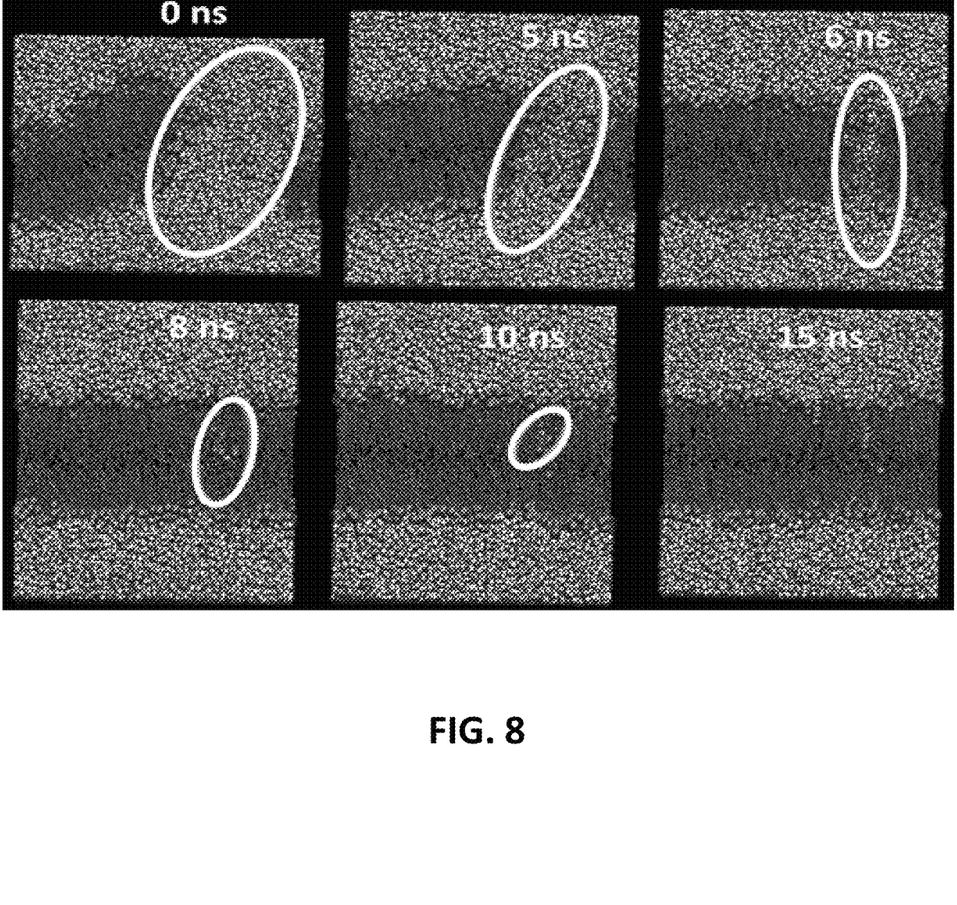
FIG. 8 shows a side view of the lipid bilayer showing reformation of the lipid bilayer in a timeline according to an embodiment of the disclosure.

The water pore disappeared completely with in first ~15-20 ns of the simulation run. The pore disappearance time were not same in all 12 simulations but pore disappearance were observed in each simulation as shown in FIG. 8.

FIG. 9 shows the snapshots of one of the system simulated along with drug molecules at sustaining electric field of 0.25 V/nm. Three out of fours molecules remained on the head group of lipid bilayer. Only one molecules entered in the water pore.

The permeation of the drug molecule through water pore was instantaneous and occurred almost in ~20 ns. Additional 200 ns MD simulation of small bilayer system (S0) were performed in presence of 4 benzoic acid molecules. During the simulation, not a single drug molecule penetrated in the lipid bilayer as shown in FIG. 9.

It was shown that the passive permeation of the benzoic acid drug molecules either not possible or it is very slow. However, on application of the sustaining electric field, the permeation happened within 20 ns as shown in FIG. 9.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein provides a system and method for in-silico design of skin electroporation. Further, the method can also be used for drug delivery.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A method for testing of skin electroporation using simulations of human skin, the method comprises a processor implemented steps of:
providing a molecular model of stratum corneum layer of the human skin, wherein the stratum corneum layer comprises a lipid bilayer;
setting a plurality of parameters for creating an equilibrium environment for the simulations;
applying an external electric field across the lipid bilayer, wherein the application of the external electric field results in the generation of a pore inside the lipid bilayer;
measuring a radius of the pore across the lipid bilayer based on the applied external electric field;
stabilizing the radius of the pore by varying the applied external electric field; and
removing the external electric field, wherein the removal of external electric field results in the reformation of the lipid bilayer and self-healing of the human skin.

2. The method of claim 1, further comprising the step of testing of a drug permeation through the pore in the presence of the external electric field.

3. The method of claim 1 further comprising the step of measuring a pore growth rate based on the applied external electric field, wherein the pore growth rate represents change in the radius of the pore in a predefined time interval.

4. The method of claim 1, wherein the radius of the pore is calculated using geometric mean of the radius of pore in the x-direction and the y-direction.

5. The method of claim 1, wherein the plurality of parameters comprises one or more of a skin temperature, pressure, force field parameters of skin lipid interaction, applied electric field or temperature coupling.

6. The method of claim 1, wherein the external electric field is applied across the bilayer of the human skin.

7. The method of claim 1, wherein the molecular model of stratum corneum layer of the skin membrane is made up of Ceramide, cholesterol and free fatty acids.

8. The method of claim 1 wherein the pore formation starts after the external electric field crosses a threshold electric field value, wherein the threshold electric field value is depending on the composition of the human skin.

9. The method of claim 1, wherein the external electric field is between 30 volts to 1500 volts.

10. The method of claim 1 further comprising the step of measuring a poration time based on the applied external electric field, wherein the poration time represents the time required for the formation of pore for the applied external electric field.

11. The method of claim 1 further comprises the step of determining an optimum value of the applied external electric field and the poration time to ensure safety of the human skin.

12. A system for testing of skin electroporation using simulations of human skin, the system comprises:
- a first input module for providing a molecular model of stratum corneum layer of the human skin, wherein the stratum corneum layer comprises a lipid bilayer;
- a second input module for setting a plurality of parameters for creating an equilibrium environment for the simulations;
- a memory; and
- a processor in communication with the memory, the processor further configured to perform the steps of:
  - applying an external electric field across the lipid bilayer, wherein the application of the external electric field results in the generation of a pore inside the lipid bilayer;
  - measuring a radius of the pore along across the lipid bilayer based on the applied external electric field;
  - stabilizing the radius of the pore by varying the applied external electric field; and
  - removing the external electric field, wherein the removal of external electric field results in the reformation of the lipid bilayer and self-healing of the human skin.

13. One or more non-transitory computer readable information medium having embodied thereon a computer program for executing a method for testing of skin electroporation using simulations of human skin, the method comprising:
- providing a molecular model of stratum corneum layer of the human skin, wherein the stratum corneum layer comprises a lipid bilayer;
- setting a plurality of parameters for creating an equilibrium environment for the simulations;
- applying an external electric field across the lipid bilayer, wherein the application of the external electric field results in the generation of a pore inside the lipid bilayer;
- measuring a radius of the pore across the lipid bilayer based on the applied external electric field;
- stabilizing the radius of the pore by varying the applied external electric field; and
- removing the external electric field, wherein the removal of external electric field results in the reformation of the lipid bilayer and self-healing of the human skin.

* * * * *